(12) United States Patent
Zaiki et al.

(10) Patent No.: US 9,801,598 B2
(45) Date of Patent: *Oct. 31, 2017

(54) X-RAY DIAGNOSTIC APPARATUS AND X-RAY DIAGNOSTIC METHOD

(71) Applicant: TOSHIBA MEDICAL SYSTEMS CORPORATION, Otawara-Shi (JP)

(72) Inventors: Ryuji Zaiki, Utsunomiya (JP); Satoshi Yamashita, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/557,784

(22) Filed: Dec. 2, 2014

(65) Prior Publication Data

US 2015/0157283 A1 Jun. 11, 2015

(30) Foreign Application Priority Data

Dec. 10, 2013 (JP) .................................. 2013-255513

(51) Int. Cl.
*A61B 6/00* (2006.01)

(52) U.S. Cl.
CPC ............ *A61B 6/4441* (2013.01); *A61B 6/504* (2013.01)

(58) Field of Classification Search
CPC .................................................. A61B 6/4441
See application file for complete search history.

(56) References Cited

U.S. PATENT DOCUMENTS

| 5,410,584 | A | 4/1995 | Schaefer et al. |
| 6,338,573 | B1* | 1/2002 | Michioka .............. F16C 19/362 |
| | | | 104/106 |
| 6,428,206 | B1 | 8/2002 | Watanabe |
| 6,461,039 | B1* | 10/2002 | Klotz ................... A61B 6/4441 |
| | | | 378/196 |
| 7,168,855 | B2 | 1/2007 | Engstrom et al. |
| 2011/0170668 | A1* | 7/2011 | Ozawa ................... A61B 6/102 |
| | | | 378/98.5 |

FOREIGN PATENT DOCUMENTS

| JP | 2000-232975 | 8/2000 |
| JP | 2001-145615 | 5/2001 |

* cited by examiner

*Primary Examiner* — Dani Fox
(74) *Attorney, Agent, or Firm* — Oblon, McClelland, Maier & Neustadt, L.L.P.

(57) ABSTRACT

According to one embodiment, an X-ray diagnostic apparatus includes a first arm, a second arm, an imaging system and a slide mechanism. The first arm rotates by a first rotating shaft and slides along with a first arc-like slide axis relatively to the first rotating shaft. The second arm rotates by a second rotating shaft fixed to the first arm and slides along with a second arc-like slide axis relatively to the second rotating shaft. The imaging system includes an X-ray generating part and an X-ray detector. The X-ray generating part and the X-ray detector are attached to the second arm. The slide mechanism slides the first arm along with the first slide axis. The slide mechanism is arranged at a position having an offset from the first rotating shaft.

12 Claims, 11 Drawing Sheets

X-RAY DIAGNOSTIC APPARATUS AND X-RAY DIAGNOSTIC METHOD

This application is based upon and claims the benefit of priority from Japanese Patent Application No. 2013-255513, filed on Dec. 10, 2013; the entire contents of which are incorporated herein by reference.

Further, the entire contents of Japanese Patent Application No. 2014-201308, filed on Sep. 30, 2014 are incorporated herein by reference.

FIELD

Embodiments described herein relate generally to an X-ray diagnostic apparatus and an X-ray diagnostic method.

BACKGROUND

In an X-ray diagnostic apparatus, an X-ray generating part and an X-ray detector facing each other are held by a C-shaped arm, for example. Especially, an X-ray diagnostic apparatus that drives a pair of an X-ray generating part and an X-ray detector using multiple arms has been proposed.

As one example, an X-ray diagnostic apparatus having a structure to arrange the first slidable arc arm, overlapped with the second slidable arc arm, on a support base which is rotatable around the first rotating axis by the first rotating shaft and to attach an end part of the third arc arm, holding an X-ray generating part and an X-ray detector, in the X-ray detector side, to the second rotating shaft included in the second arc arm, has been proposed.

In the X-ray diagnostic apparatus having this structure, the X-ray generating part and the X-ray detector can be positioned by the two rotating shafts, which consist of not only the first rotating shaft, fixed on the support base, in the horizontal or vertical direction but also the second rotating shaft parallel to the X-ray exposure direction. Moreover, the X-ray generating part and the X-ray detector can also be positioned by the respective slide operations of the first arc arm and the second arc arm.

As another example, an X-ray diagnostic apparatus, which has a structure to suspend the first arc arm on a ceiling so as to rotate around the first rotating axis by the first rotating shaft, to have the second rotating shaft at one end of the first arc arm sliding along an arc track, and to attach a nearly middle part of the second arc arm, which holds an X-ray generating part and an X-ray detector at its both ends, to the second rotating shaft, has been proposed. In the X-ray diagnostic apparatus having this structure, the X-ray generating part and the X-ray detector can be positioned by the first rotating shaft fixed on the ceiling, the slide operation of the first arc arm, and the second rotating shaft.

In the X-ray diagnostic apparatus, it is desired to enable imaging from various directions, such as a 3D (three dimensional) imaging, an imaging of an obliquely travelling blood vessel, or the like.

Accordingly, an object of the present invention is to provide an X-ray diagnostic apparatus and an X-ray diagnostic method which can easily perform various kinds of imaging, such as 3D imaging, imaging of an obliquely travelling blood vessel, or the like.

DETAILED DESCRIPTION

In general, according to one embodiment, an X-ray diagnostic apparatus includes a first arm, a second arm, an imaging system and a slide mechanism. The first arm rotates by a first rotating shaft and slides along with a first arc-like slide axis relatively to the first rotating shaft. The second arm rotates by a second rotating shaft fixed to the first arm and slides along with a second arc-like slide axis relatively to the second rotating shaft. The imaging system includes an X-ray generating part and an X-ray detector. The X-ray generating part and the X-ray detector are attached to the second arm. The slide mechanism slides the first arm along with the first slide axis. The slide mechanism is arranged at a position having an offset from the first rotating shaft.

Further, according to another embodiment, an X-ray diagnostic method includes: driving a first arm rotating by a first rotating shaft and sliding along with a first arc-like slide axis relatively to the first rotating shaft; driving a second arm rotating by a second rotating shaft fixed to the first arm and sliding along with a second arc-like slide axis relatively to the second rotating shaft; and imaging an object using an imaging system including an X-ray generating part and an X-ray detector. The X-ray generating part and the X-ray detector are attached to the second arm. The first arm is slid along with the first slide axis by a slide mechanism arranged at a position having an offset from the first rotating shaft.

An X-ray diagnostic apparatus and an X-ray diagnostic method according to embodiments of the present invention will be described with reference to the accompanying drawings.

First Embodiment

Figure 1:
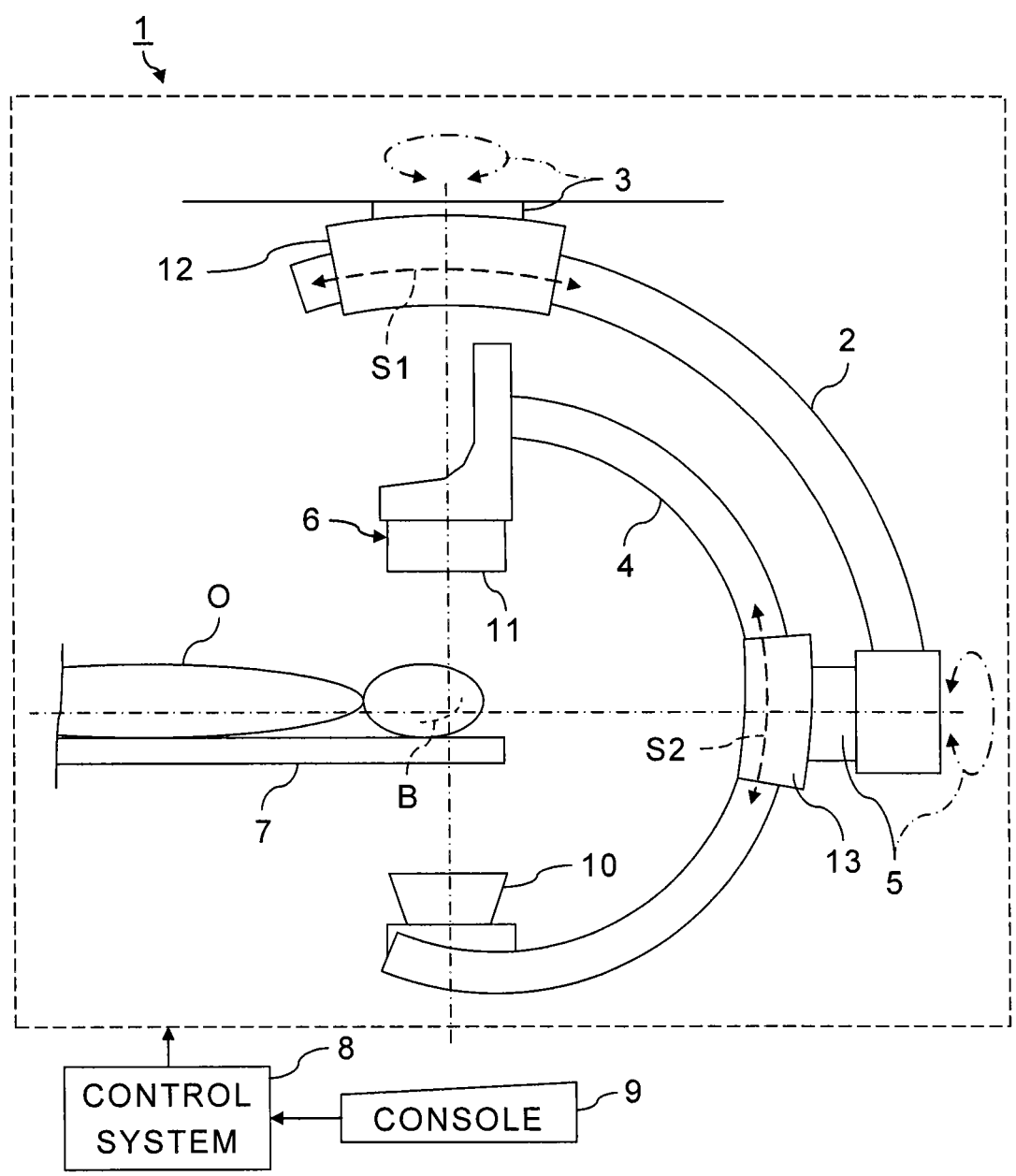
FIG. 1 is a structural view of an X-ray diagnostic apparatus according to the first embodiment of the present invention.

FIG. 1 is a structural view of an X-ray diagnostic apparatus according to the first embodiment of the present invention.

An X-ray diagnostic apparatus 1 includes the first arm 2, the first rotating shaft 3, the second arm 4, the second rotating shaft 5, an imaging system 6, a bed 7, a control system 8, and a console 9. The imaging system 6 has an X-ray generating part 10 and an X-ray detector 11.

The first arm 2 can be rotated around the first rotating axis by the first rotating shaft 3. The first arm 2 can be attached to a ceiling using the first rotating shaft 3 as a support post, as illustrated. Therefore, henceforth, the first arm 2 is called a support post side arm 2 while the first rotating shaft 3 is called a support post circling shaft 3.

The support post side arm 2 is configured to slide relatively to the support post circling shaft 3 along with the first arc slide axis S1 by the first slide mechanism 12. Therefore, a form of the support post side arm 2 may be also arc-like. Henceforth, the first slide axis S1 is called a support post side arc slide axis S1 while the first slide mechanism 12 is called a support post side arm slide mechanism 12.

On the other hand, the second arm 4 can be rotated around the second rotating axis by the second rotating shaft 5. The imaging system 6 is attached to the second arm 4. Typically, the X-ray generating part 10, having an X-ray tube for exposing an X-ray toward an object O, is fixed to one end of the second arm 4 while the X-ray detector 11 is fixed to the other end of the second arm 4 so that the X-ray detector 11 faces to the X-ray generating part 10 across the object O set on the bed 7, as illustrated. Therefore, the second arm 4 is C-shaped. Henceforth, the second arm 4 is called a C-shaped arm 4 while the second rotating shaft 5 is called a C-shaped arm main rotating shaft 5.

The C-shaped arm 4 is configured to slide along the second arc slide axis S2, relative to the C-shaped arm main rotating shaft 5, by the second slide mechanism 13. Hereafter, the second slide axis S2 is called a C-shaped arm slide axis S2, and the second slide mechanism 13 is called a C-shaped arm slide mechanism 13. By driving the C-shaped arm 4 in the direction of the C-shaped arm slide axis S2, the C-shaped arm 4 can be rotated like a propeller, around a desired position of the C-shaped arm 4 as a rotating axis, by the C-shaped arm main rotating shaft 5.

The C-shaped arm main rotating shaft 5 for rotating the C-shaped arm 4 is fixed to the support post side arm 2. Therefore, the C-shaped arm main rotating shaft 5 itself can be moved along the support post side arc slide axis S1 with the C-shaped arm 4. In addition, the C-shaped arm 4 and the C-shaped arm main rotating shaft 5 can be rotated around the support post circling axis by the support post circling shaft 3 with the support post side arm 2. Consequently, the C-shaped arm 4 and the C-shaped arm main rotating shaft 5 can be inclined with an arbitrary angle. Note that, it is desirable that an attachment position of the C-shaped arm main rotating shaft 5 to the support post side arm 2 should be an end part of the support post side arm 2 from a viewpoint of preventing the end part of the support post side arm 2 from obstructing surrounding devices and causing interference.

On the other hand, the support post side arm slide mechanism 12 is directly or indirectly connected with the support post circling shaft 3 prepared on a ceiling. Therefore, the support post circling shaft 3 connected with the support post side arm slide mechanism 12 doubles as the first holding part for hanging both the support post side arm 2 and the C-shaped arm 4 on the ceiling. Meanwhile, the second holding part for holding the C-shaped arm main rotating shaft 5 is formed in the support post side arm 2. As mentioned above, it is desirable that the second holding part should be formed in the end part of the support post side arm 2 from a viewpoint of preventing interference.

Figure 2:
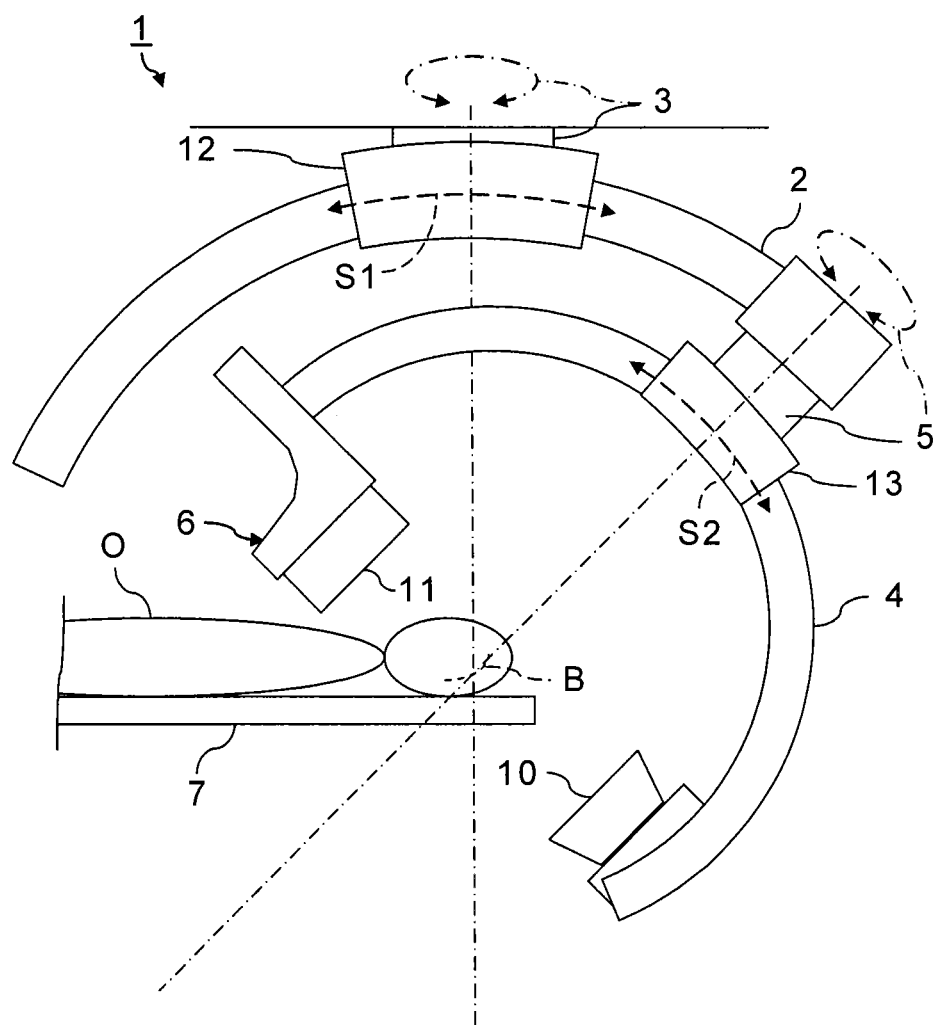
FIG. 2 is a view showing an example of inclining the C-shaped arm main rotating shaft shown in FIG. 1 according to an imaging section of an object.

FIG. 2 is a view showing an example of inclining the C-shaped arm main rotating shaft 5 shown in FIG. 1 according to an imaging section of an object O.

When the support post side arm slide mechanism 12 and the support post circling shaft 3 are operated, the C-shaped arm main rotating shaft 5 can be inclined with an arbitrary angle as shown in FIG. 2. Consequently, even when a blood vessel B which travels obliquely to the horizontal direction inside an imaging part, such as a brain or a heart, is a treatment target, the C-shaped arm main rotating shaft 5 can be positioned so as to be in parallel to the traveling direction of the obliquely travelling blood vessel B.

Then, the C-shaped arm 4 can be rotated around an isocenter (treatment center) axis like a propeller in a condition that the C-shaped arm main rotating shaft 5 has been set in the perpendicular direction to a section of the oblique travelling blood vessel B. That is, the imaging system 6 including the X-ray generating part 10 and the X-ray detector 11 can be rotated around the isocenter axis, which inclines relative to a body axis of an object O, by a rotation operation of the C-shaped arm main rotating shaft 5, so that the locus of the imaging system 6 becomes a circle. Thereby, the imaging system 6 can acquires X-ray images, of an object O, on which a form of an inclining part of interest, such as an obliquely travelling blood vessel B, can be observed easily.

When the support post side arc slide axis S1 and the C-shaped arm slide axis S2 are positioned on a same plane by rotation operations of the support post circling shaft 3 and the C-shaped arm main rotating shaft 5, the support post side arc slide axis S1 and the C-shaped arm slide axis S2 become concentric. Therefore, the range of the possible circling angle, on a same plane, of the C-shaped arm 4 can be a range obtained by adding a movable range of the support post side arm slide mechanism 12 to a movable range of the C-shaped arm slide mechanism 13.

Arbitrary structures can be adopted as the support post side arm slide mechanism 12 for sliding the support post side arm 2 along the support post side arc slide axis S1 and as the C-shaped arm slide mechanism 13 for sliding the C-shaped arm 4 along the C-shaped arm slide axis S2. Typically, a slide guide mechanism in which cylindrical wheels run on arc-like curving rails can be used for one or both of the support post side arm slide mechanism 12 and the C-shaped arm slide mechanism 13.

However, the loads of the imaging system 6, the C-shaped arm 4, the C-shaped arm main rotating shaft 5, and the support post side arm 2 are born by the support post side arm slide mechanism 12. Therefore, adopting a structure having a high rigidity as the support post side arm slide mechanism 12 leads to improvement of an image quality by suppressing vibration.

Figure 3:
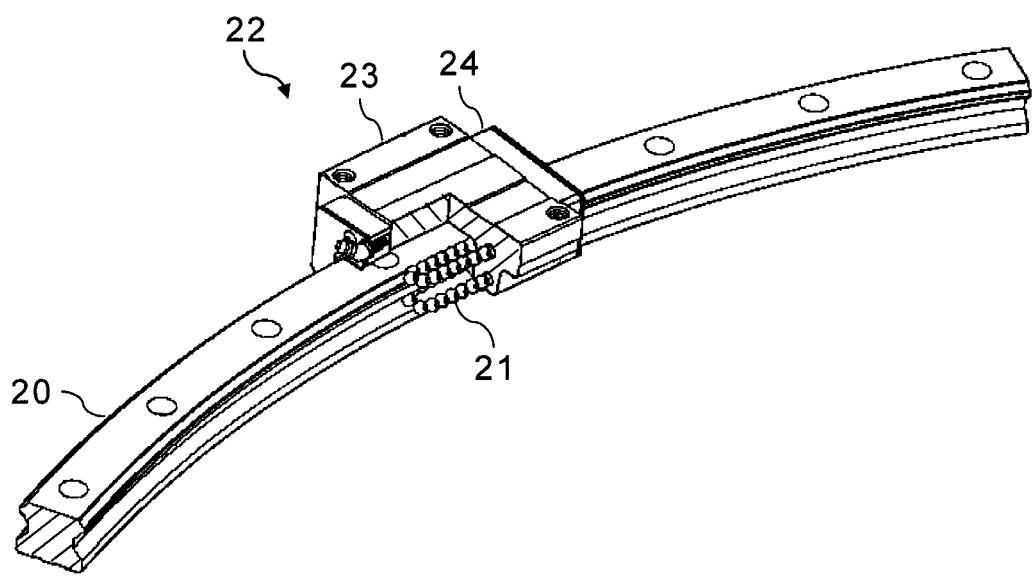
FIG. 3 is a perspective view showing an example of slide mechanism which can be adopted as the support post side arm slide mechanism and the C-shaped arm slide mechanism shown in FIG. 1.

FIG. 3 is a perspective view showing an example of slide mechanism which can be adopted as the support post side arm slide mechanism 12 and the C-shaped arm slide mechanism 13 shown in FIG. 1.

As shown in FIG. 3, a slide guide mechanism 22 having a holding structure that multiple balls 21 roll on an arc rail 20 can be used for one or both of the support post side arm slide mechanism 12 and the C-shaped arm slide mechanism 13. When at least the support post side arm 2 is configured to slide along the support post side arc slide axis S1 using the slide guide mechanism 22, which has the holding structure having the multiple rolling balls 21 as show in FIG. 3, the loads put to the support post side arm 2 can satisfactorily be counteracted. That is, a sufficient rigidity can be attained when the slide guide mechanism 22 having the holding structure including the multiple rolling balls 21 is adopted as at least the support post side arm slide mechanism 12.

Especially, when the slide guide mechanism 22 has a holding structure that the multiple balls 21 roll on each of bearing planes formed on the four corners of the rail 20 as illustrated in FIG. 3, the equal loads can be put to the rail 20 from the four directions.

The slide guide mechanism 22 illustrated in FIG. 3 has a holding structure that a part of the multiple circulating balls 21 roll on the rail 20. Specifically, through-holes have been formed, as pathways for circulating the multiple balls 21, in a holding block 23 which slides along the rail 20. Moreover, in order to guide the balls 21 rolling from the through-holes of the holding block 23 to the pathways, of the balls 21, formed as interspaces between the bearing planes of the rail 20 and the holding block 23, end plates 24 have been prepared at the both sides of the holding block 23. Owing to such a structure of the slide guide mechanism 22, smooth slides and suppression of galling of the holding block 23 can be attained.

When the slide guide mechanism 22 as shown in FIG. 3 is also adopted to the C-shaped arm slide mechanism 13, its size can become smaller compared with the case of adopting the conventional slide mechanism having the structure in which cylindrical wheels run. Consequently, it can contribute to reduction of interference. On the contrary, the conventional slide mechanism having the structure that cylindrical wheels run may be adopted to the C-shaped arm slide mechanism 13 whose loads are relatively small. In that case, simplification of the structure and cost reduction of the C-shaped arm slide mechanism 13 can be attained.

Moreover, determination of the slide operation range of the support post side arm slide mechanism 12 allows reduction in rotary torque required for drive of the support post side arm slide mechanism 12. Specifically, by setting the slide range of the support post side arm 2 along the support post side arc slide axis S1 to be shorter than the slide range of the C-shaped arm 4 along the C-shaped arm slide axis S2, a moving speed required for operation of the support post side arm slide mechanism 12 can be slower than a moving speed of the C-shaped arm slide mechanism 13 according to the ratio of the slide operation ranges. Consequently, the reduction of the rotary torque required for drive of the support post side arm slide mechanism 12 can be attained.

Figure 4:
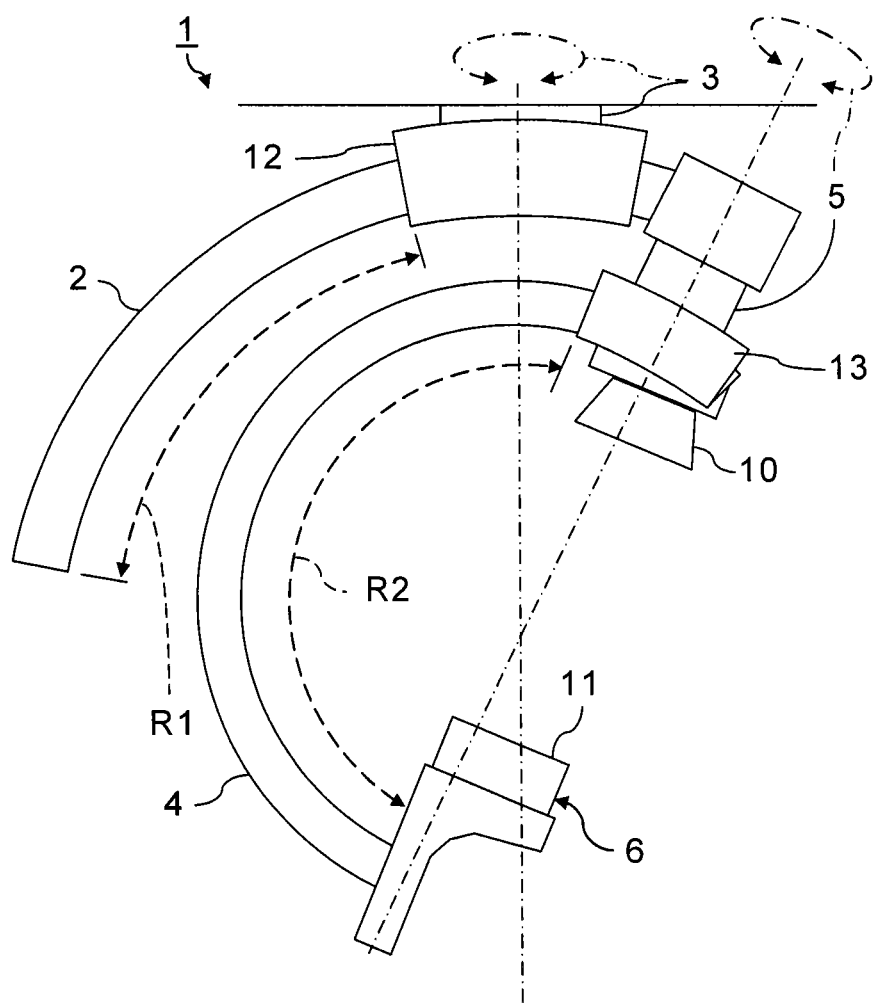
FIG. 4 is a view showing an example of the C-shaped arm rotated by slide operations by the support post side arm slide mechanism and in the C-shaped arm slide axis which show in FIG. 1.

FIG. 4 is a view showing an example of the C-shaped arm 4 rotated by slide operations by the support post side arm slide mechanism 12 and in the C-shaped arm slide axis S2 which show in FIG. 1.

As shown in FIG. 4, a rotation range of the C-shaped arm 4 in the direction of the C-shaped arm slide axis S2 can be longer than a movable range of the C-shaped arm slide mechanism 13 by the slide operations of both the support post side arm slide mechanism 12 and the C-shaped arm slide mechanism 13.

However, the loads of the imaging system 6, the C-shaped arm 4, the C-shaped arm main rotating shaft 5, and the support post side arm 2 are put to the support post side arm slide mechanism 12, as mentioned above. Therefore, the rotary torque for sliding the support post side arm 2 becomes larger than the rotary torque for sliding the C-shaped arm 4.

Accordingly, as shown in FIG. 4, a slide operation range R1 of the support post side arm 2 by the support post side arm slide mechanism 12 can be set to 40 degrees while a slide operation range R2 of the C-shaped arm 4 by the C-shaped arm slide mechanism 13 can be set to 160 degrees, for example. That is, a possible rotation angle range of the support post side arm 2 in the support post side arc slide axis S1 direction can be set to about ¼ of a possible rotation angle range of the C-shaped arm 4 in the C-shaped arm slide axis S2 direction.

Then, the moving speed of the support post side arm slide mechanism 12 becomes about ¼ of the moving speed of the C-shaped arm slide mechanism 13. Thereby, it is possible to slide the support post side arm 2, having a larger rotational torque than that of the C-shaped arm 4, using a drive power supply similar to a drive power supply for sliding the C-shaped arm 4 by the C-shaped arm slide mechanism 13.

That is, by limiting the slide operation range of the support post side arm 2 by the support post side arm slide mechanism 12, the support post side arm slide mechanism 12 can be driven using a general and practical drive power supply and drive mechanism. Note that, as an example of general drive mechanism to drive each of the C-shaped arm slide mechanism 13 and the support post side arm slide mechanism 12, a drive mechanism consisting of a servomotor and a worm speed reducer can be mentioned. Moreover, an arbitrary known drive mechanism can be used for the slide drive mechanism whether it is a slide guide mechanism by running of wheels or a slide guide mechanism by circulating and rolling of the balls 21 as shown in FIG. 3.

The control system 8 performs imaging of an object O using the imaging system 6 by driving and controlling the support post side arm 2, the C-shaped arm 4, and the imaging system 6. Specifically, the support post circling shaft 3 and the support post side arm slide mechanism 12 are driven by control signals from the control system 8. Thereby, the support post side arm 2 can be positioned. Similarly, the C-shaped arm main rotating shaft 5 and the C-shaped arm slide mechanism 13 are driven by control signals from the control system 8. Thereby, the C-shaped arm 4 can be positioned. Furthermore, an X-ray can be exposed toward an object O by applying a voltage to the X-ray generating part 10 from a high voltage generating device included in the control system 8. In addition, the control system 8 has other devices required for imaging, such as a drive device to drive the bed 7. Moreover, direction information to be input into the control system 8 can be input from the console 9.

Especially, the control system 8 is configured to control the support post side arm 2, the C-shaped arm 4, and the imaging system 6 in the first mode and the second mode which can be mutually switched. The first mode is an independent operational mode, in which each movement of the support post side arm 2 and the C-shaped arm 4 is started and stopped by an independent slide operation. Meanwhile, the second mode is an interlocking operational mode, in which movements by slide operations of the support post side arm 2 and the C-shaped arm 4 are started simultaneously at a movement start time of the imaging system 6, and the support post side arm 2 and the C-shaped arm 4 are stopped simultaneously at a stop time of the imaging system 6. An selection of an operational mode can be performed by inputting direction information from the console 9 into the control system 8.

The independent operational mode to independently operate each of the support post side arm 2 and the C-shaped arm 4 can be chosen mainly for imaging of an inclining imaging part as shown in FIG. 2. Meanwhile, the interlocking operational mode to operate the support post side arm 2 and the C-shaped arm 4 with interlocking can be chosen mainly in a case, such as 3D imaging, that imaging is performed by exposing X-rays towards an object O from multiple directions in an angle range of not less than 180 degrees. That is, when a movement area of the imaging system 6 by slide operations is wide, the interlocking operational mode can be chosen.

In a case that the imaging system 6 is rotated by not less than 180 degrees on the plane including the C-shaped arm main rotating shaft 5, both the C-shaped arm 4 and the support post side arm 2 slide in the plane including the C-shaped arm main rotating shaft 5, as mentioned above. It is also possible to slide both the C-shaped arm 4 and the support post side arm 2 with operating one or both of the support post circling shaft 3 and the C-shaped arm main rotating shaft 5.

Thus, in a case that both the C-shaped arm slide mechanism 13 and the support post side arm slide mechanism 12 are in operations, the moving speeds of the C-shaped arm 4 and the support post side arm 2 can be controlled so that one of the C-shaped arm 4 and the support post side arm 2 would not stop while the other is being driven, and contrarily, so that one of the C-shaped arm 4 and the support post side arm 2 would not start its drive prior to the other.

In this case, the moving speeds of the C-shaped arm 4 and the support post side arm 2 are controlled according to the slide range of the C-shaped arm 4 and the slide range of the support post side arm 2, so that the timings when the C-shaped arm 4 and the support post side arm 2 start movements from their start positions by slide operations accord to each other, and also, so that their arrival timings at stop positions accord to each other. Therefore, when a slide distance of the C-shaped arm 4 differs from a slide distance of the support post side arm 2, the movement speed of the C-shaped arm 4 is different from the movement speed of the support post side arm 2.

As a specific example, in the case that the slide range of the C-shaped arm 4 is 160 degrees and the slide range of the support post side arm 2 is 40 degrees, the movement speed of the support post side arm 2 should be set to one fourth of the movement speed of the C-shaped arm 4. For example, when the angular velocity of the C-shaped arm 4 is 40 degrees/second, the angular velocity of the support post side arm 2 should be set to 10 degrees/second.

Such a speed control allows avoiding discontinuous operations of the C-shaped arm 4 and the support post side arm 2 in all the slide operation ranges. That is, both the C-shaped arm 4 and the support post side arm 2 can be operated continuously from their moving starts to stops. Thereby, vibration due to an inertia load arising when one of the C-shaped arm 4 and the support post side arm 2 starts or stops at a timing different from that of the other can be avoided. As a result, vibration and image quality deterioration of 3D images because of the vibration can be reduced.

That is, the X-ray diagnostic apparatus 1 as mentioned above is an apparatus which has the two arms of the C-shaped arm 4 and the support post side arm 2 for positioning the imaging system 6, and move the imaging system 6 along the four axes of the center of the support post circling shaft 3, the support post side arc slide axis S1, the center of the C-shaped arm main rotating shaft 5, and the C-shaped arm slide axis S2.

Therefore, the X-ray diagnostic apparatus 1 can be used as an apparatus for circulatory organs. Especially, according to the X-ray diagnostic apparatus 1, the C-shaped arm main rotating shaft 5 can be inclined according to a part of interest, such as an inclining blood vessel. For example, a rotation of the support post circling shaft 3 and a slide operation of the support post side arm 2 in the support post side arc slide axis S1 direction can set the C-shaped arm main rotating shaft 5 to be in parallel to a traveling direction of an arbitrary blood vessel which travels in a certain direction in a brain or a heart. Then, not only rotation imaging around a body axis of an object O but also rotation imaging around an inclining isocenter axis can be performed. Typically, rotation imaging around the direction perpendicular to a section of an inclining blood vessel can be performed. Thereby, X-ray images appropriate for understanding a form of a blood vessel can be acquired.

In addition, according to the X-ray diagnostic apparatus 1, the imaging system 6 can be moved within a large range. Especially, the imaging system 6 can be moved within a large range to cope with 3D imaging fully, using both the slide of the support post side arm 2 in the support post side arc slide axis S1 direction and the slide of the C-shaped arm 4 in the C-shaped arm slide axis S2 direction together. That is, a movement of the imaging system 6 over the slide range of the C-shaped arm 4 by the C-shaped arm slide mechanism 13 can be attained. Moreover, it is possible to perform a movement of the imaging system 6, which has been conventionally difficult, such as a slide of the C-shaped arm 4 in the C-shaped arm slide axis S2 direction in a condition that the X-ray generating part 10 and the X-ray detector 11 have been arranged at the right side and the left side of an object O. Therefore, a moving range of the imaging system 6 required for 3D imaging can fully be covered.

Second Embodiment

Figure 5:
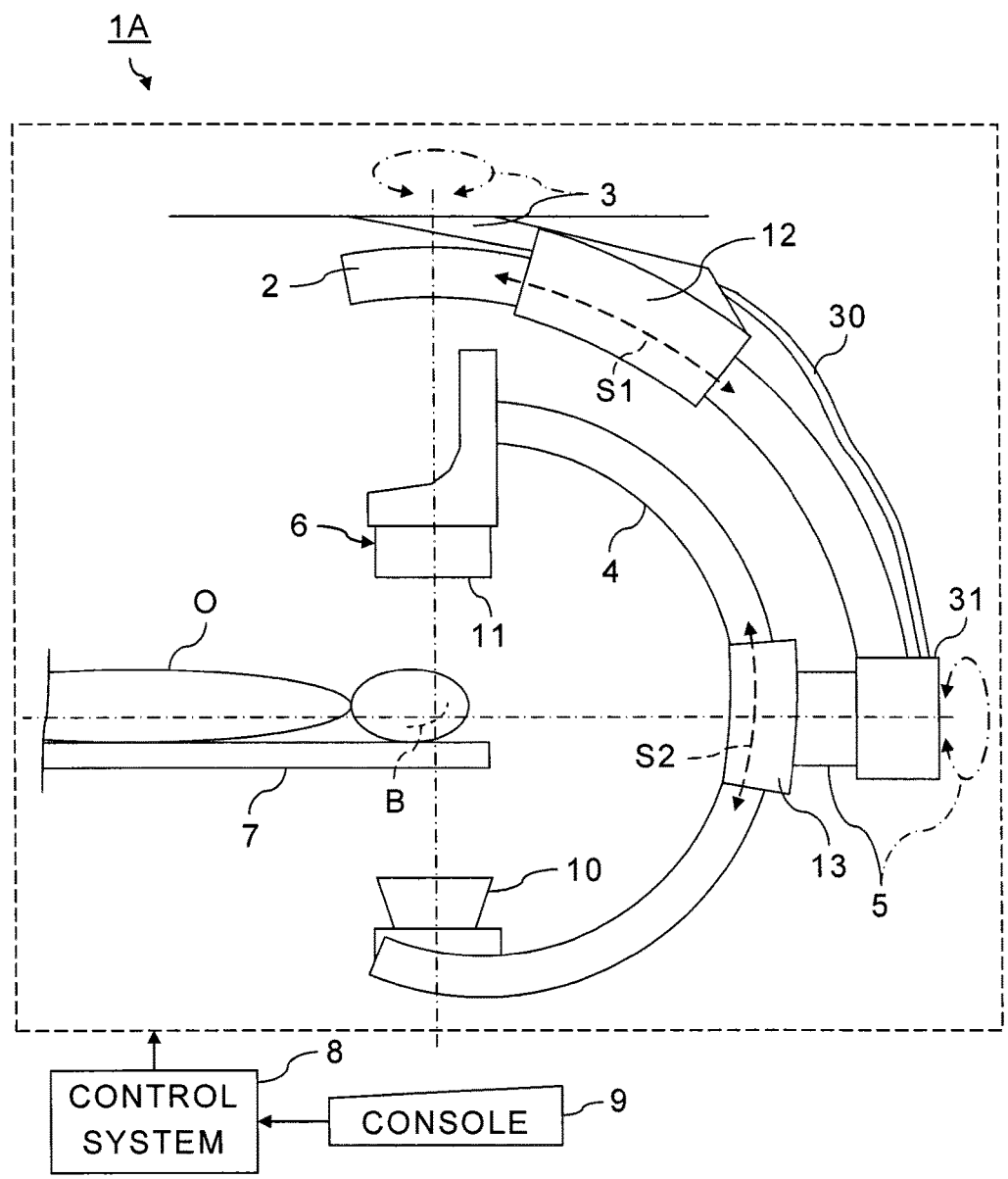
FIG. 5 is a structural view of an X-ray diagnostic apparatus according to the second embodiment of the present invention.

FIG. 5 is a structural view of an X-ray diagnostic apparatus according to the second embodiment of the present invention.

The X-ray diagnostic apparatus 1A in the second embodiment shown in FIG. 5 is different from the X-ray diagnostic apparatus 1 in the first embodiment in point that the support post side arm slide mechanism 12 for sliding the support post side arm 2 along with the support post side arc slide axis S1 is arranged so that the center position of the support post side arc slide axis S1 formed on the support post side arm slide mechanism 12 lies on a position having an offset from the support post circling shaft 3. Since other configurations and actions of the X-ray diagnostic apparatus 1A in the second embodiment do not differ from those of the X-ray diagnostic apparatus 1 in the first embodiment substantially, same signs are attached to the same elements and explanation thereof is omitted.

The support post side arm slide mechanism 12 of the X-ray diagnostic apparatus 1A is arranged at a position where is not directly beneath the support post circling shaft 3 hung on a ceiling but has an offset, in a direction perpendicular to the support post circling shaft 3, from the center of the support post circling shaft 3. Therefore, the support post side arm slide mechanism 12 rotates around the support post circling axis, which is the center of the support post circling shaft 3, through a circular track whose center is the center of the support post circling shaft 3.

In the second embodiment, the support post side arm slide mechanism 12 is also directly or indirectly connected with the support post circling shaft 3 prepared on the ceiling. Therefore, the support post circling shaft 3 doubles the first holding part for hanging both the support post side arm 2 and the C-shaped arm 4 on the ceiling by being connected with the support post side arm slide mechanism 12.

Meanwhile, in the support post side arm 2, a rotating shaft holding part 31 for holding the C-shaped arm main rotating shaft 5 is formed as the second holding part. As well as the first embodiment, it is desirable that the rotating shaft holding part 31 is formed in an end part of the support post side arm 2 from a viewpoint of preventing interference. Therefore, in the example shown in FIG. 5, the rotating shaft holding part 31 holding the C-shaped arm main rotating shaft 5 has been connected with the end face, of the support post side arm 2, which intersects with the support post side arc slide axis S1.

Figure 6:
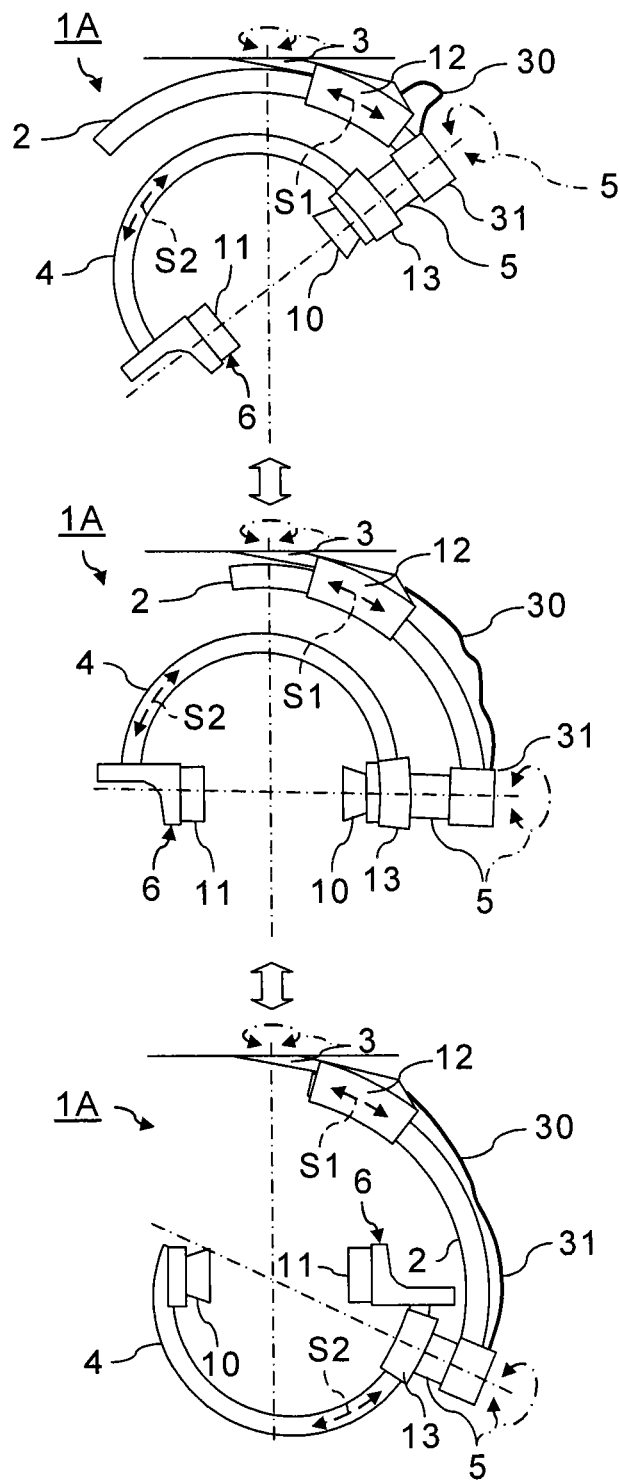
FIG. 6 is a view showing an operation of the X-ray diagnostic apparatus shown in FIG. 5.

FIG. 6 is a view showing an operation of the X-ray diagnostic apparatus 1A shown in FIG. 5.

As shown in FIG. 6, a wide stroke range of the imaging system 6 can be secured by driving the support post side arm slide mechanism 12 and the C-shaped arm slide mechanism 13. Especially, it is desirable to arrange the support post side arm slide mechanism 12 so that the support post side arm slide mechanism 12 holds a part, which is not considered to be the end part, of the support post side arm 2, in the condition that the C-shaped arm main rotating shaft 5 is perpendicular to the support post circling shaft 3, as illustrated. In other words, when the position of the support post side arm 2 in the condition that the C-shaped arm main rotating shaft 5 is nearly perpendicular to the support post circling shaft 3 is set to be the initial position, it is desired to arrange the support post side arm slide mechanism 12 so that the end part, of the support post side arm 2 at the initial position, in the support post circling shaft 3 side protrudes from the support post side arm slide mechanism 12.

When the support post side arm slide mechanism 12 is arranged as mentioned above, the end part, in the support post circling shaft 3 side, of the support post side arm 2 at the initial position can approach the ceiling side closer. That is, when the relative position of the support post side arm slide mechanism 12 to the ceiling is constant, the support post side arm 2 can approach the ceiling side closer. In addition, the support post side arm slide mechanism 12 itself can also approach the ceiling closer compared with the case of arranging the support post side arm slide mechanism 12 at the tip of the support post circling shaft 3. As a result, even in a case that a ceiling of an imaging room is low, the X-ray diagnostic apparatus 1A can be installed.

In addition, when the support post side arm 2 is at the initial position, the support post side arm 2 and the C-shaped arm main rotating shaft 5 can be moved both in the positive direction and in the negative direction of the support post side arc slide axis S1 direction. That is, the support post side arm 2 and the C-shaped arm main rotating shaft 5 can be moved to the both sides of the positive direction and the negative direction from the initial position in the support post side arc slide axis S1 direction.

Figure 7:
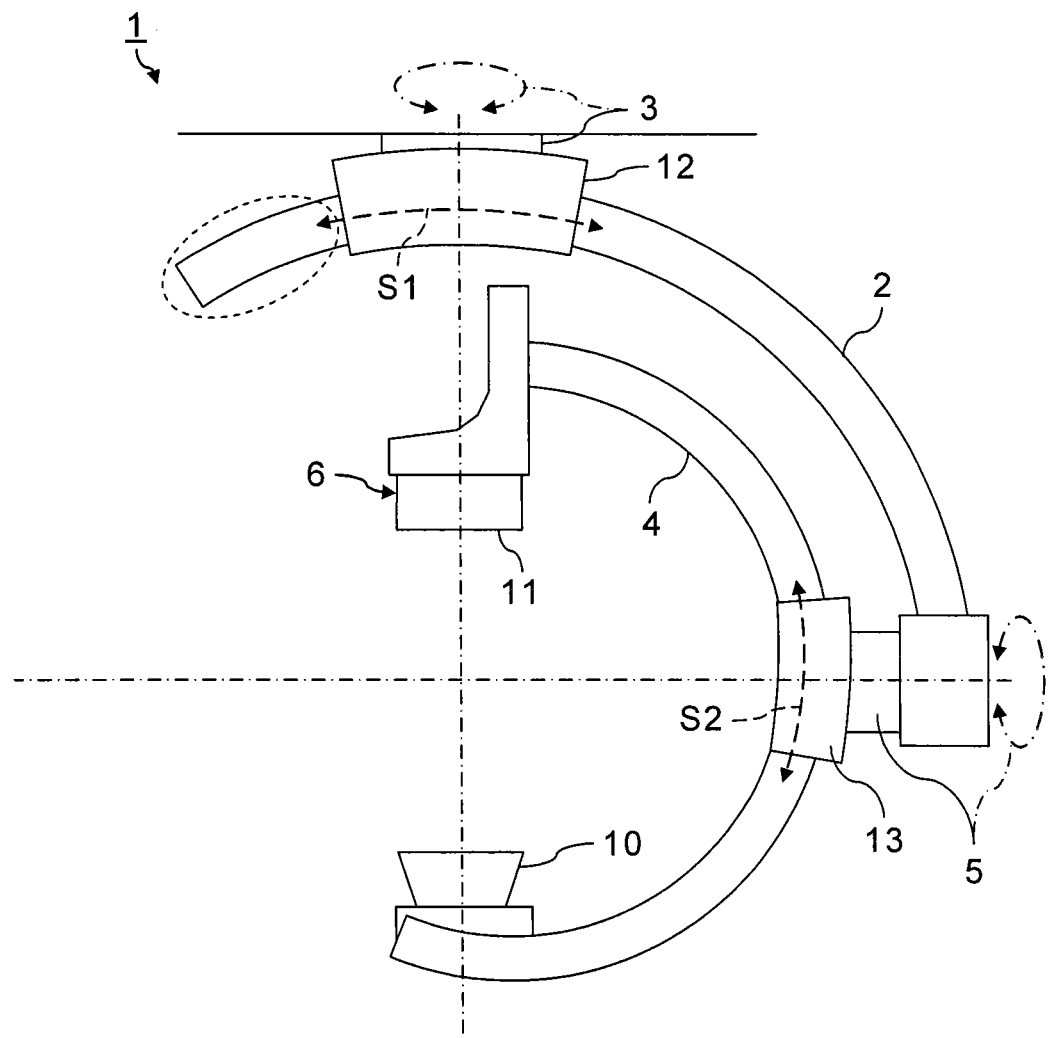
FIG. 7 is a view showing an example case where the support post side arm of the X-ray diagnostic apparatus shown in FIG. 1 is configured to be able to move from an initial position to both the positive direction and the negative direction in the support post side arc slide axis.

FIG. 7 is a view showing an example case where the support post side arm 2 of the X-ray diagnostic apparatus 1 shown in FIG. 1 is configured to be able to move from an initial position to both the positive direction and the negative direction in the support post side arc slide axis S1.

When the stroke range of the support post side arm 2, in the support post side arc slide axis S1 direction, included in the X-ray diagnostic apparatus 1 shown in FIG. 1 is prepared in the both sides from the initial position, the end part of the support post side arm 2 at the initial position protrudes from the center of the support post circling shaft 3, as shown with a dotted line frame in FIG. 7.

On the contrary, even when the stroke range of the support post side arm 2, in the support post side arc slide axis S1 direction, included in the X-ray diagnostic apparatus 1A shown in FIG. 5 is prepared in the both sides of the initial position, the support post side arm 2 at the initial position does not protrude from the center of the support post circling shaft 3. Moreover, even when the support post side arm 2 slides, a protruding length of the support post side arm 2 from the center of the support post circling shaft 3 can be shortened.

That is, in the X-ray diagnostic apparatus 1A, the stroke range of the support post side arm 2 from the initial position can be secured in the both sides in the support post side arc slide axis S1 direction, and at the same time, an extreme protrusion of the support post side arm 2 from the center of the support post circling shaft 3 can be avoided. Consequently, interference of the support post side arm 2 with surrounding devices can be minimized.

Moreover, when the support post side arm slide mechanism 12 is arranged so that the support post side arm slide mechanism 12 holds a part, which is not considered to be the end part of the support post side arm 2 at the initial position, the required length of cables 30 can be shortened.

Specifically, slacks for covering the movable range of the support post side arm 2 in the support post side arc slide axis S1 direction are required for the cables 30 which connect components, such as the support post side arm slide mechanism 12 and the support post circling shaft 3, static in the support post side arc slide axis S1 direction, with the rotating shaft holding part 31 and the C-shaped arm slide mechanism 13 holding the C-shaped arm main rotating shaft 5. Therefore, by configuring the support post side arm slide mechanism 12 so as to hold a part that is not considered to be the end part of the support post side arm 2, the lengths of the cables 30 can be shortened compared with the case of configuring the support post side arm slide mechanism 12 to hold the end part of the support post side arm 2.

Especially, when the support post side arm slide mechanism 12 is configured to hold the part considered to be the center position of the movable range of the support post side arm 2 at the initial position, the lengths of slacks required for the cables 30 can be shortened into about half, compared with the case that the support post side arm slide mechanism 12 is configured to hold the end part of the support post side arm 2. In addition, the protruding length of the support post side arm 2 from the center of the support post circling shaft 3 can be shortened as mentioned above.

That is, the X-ray diagnostic apparatus 1A mentioned above is to arrange the support post side arm slide mechanism 12, which is composed of balls or rollers, not at a position just beneath a ceiling but at a position shifted from the center of the support post circling shaft 3.

Consequently, in the X-ray diagnostic apparatus 1A, components, such as balls or rollers, included in the support post side arm slide mechanism 12 do not exist between the ceiling and the highest part of the support post side arm 2 at the initial position, which is the end part in the ceiling side. Therefore, even in a low ceiling room, the support post side arm 2 and the C-shaped arm 4 do not interfere with a floor, and the X-ray diagnostic apparatus 1A can be installed safely. Specifically, by making an offset between a position of the support post side arm slide mechanism 12 and the center of the support post circling shaft 3 as illustrated in FIG. 5, the tip of the support post side arm 2 can approach the ceiling closer, compared with the case that the support post side arm slide mechanism 12 is arranged at the highest part near the center of the support post circling shaft 3 as shown in FIG. 1. Consequently, the X-ray diagnostic apparatus 1A can be installed even in an imaging room whose ceiling is low.

Moreover, the protruding length of the support post side arm 2 from the support post side arm slide mechanism 12 can be minimized with securing the movable directions from the initial position of the support post side arm 2 in the both sides of the support post side arm slide mechanism 12. As a result, interferences by the support post side arm 2 with a shadowless light and surrounding devices can be avoided. In addition, the lengths of the play parts of the cables 30 required to cover the movable range of the support post side arm 2 can be shortened.

Note that, as a structure of the support post side arm slide mechanism 12 in the second embodiment, not only the structure that the multiple balls 21 roll on the four corners of the arc rail 20 as illustrated in FIG. 3 but also various structures can be adopted.

Figure 8:
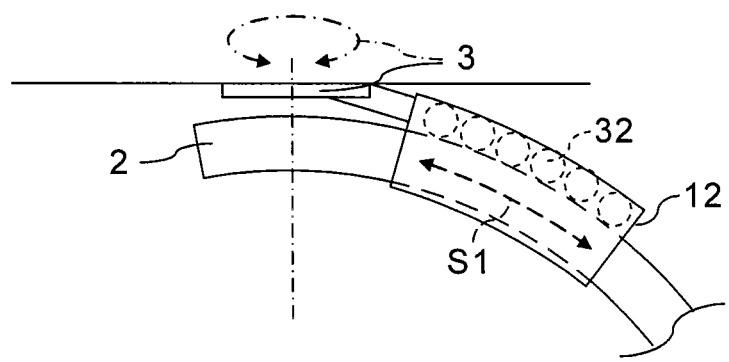
FIG. 8 is a view showing the first structural example of the support post side arm slide mechanism shown in FIG. 5.

FIG. 8 is a view showing the first structural example of the support post side arm slide mechanism 12 shown in FIG. 5.

As shown in FIG. 8, a slung type structure, of which rollers 32 for sliding the support post side arm 2 along the support post side arc slide axis S1 have been arranged only in the upper side of the support post side arm 2, can be adopted as the structure of the support post side arm slide mechanism 12. In this case, the required distance between a ceiling and the highest part of the support post side arm 2 can be shortened with reducing the rigidities required for the support post circling shaft 3, the support post side arm slide mechanism 12, and the like by avoiding increase in weight of the support post side arm slide mechanism 12.

Figure 9:
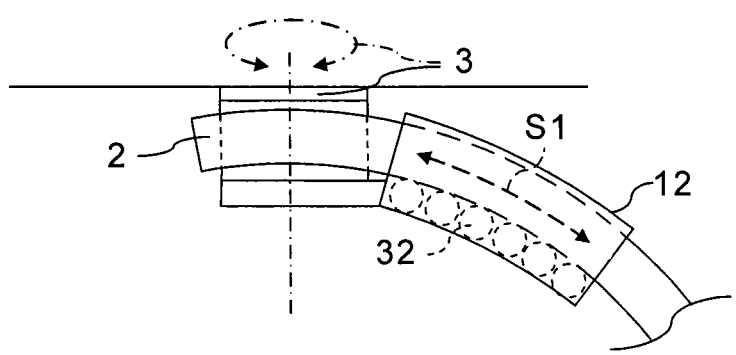
FIG. 9 is a view showing the second structural example of the support post side arm slide mechanism shown in FIG. 5.
Figure 10:
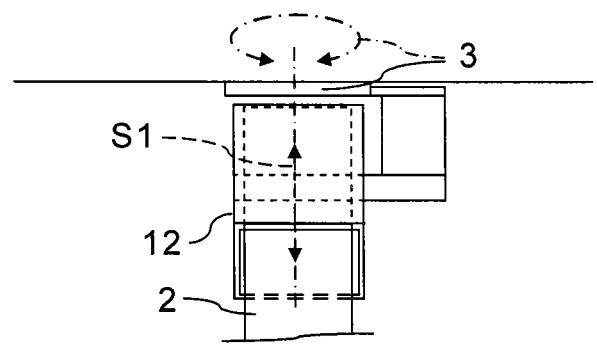
FIG. 10 is a right side view of the support post side arm slide mechanism shown in FIG. 9.

FIG. 9 is a view showing the second structural example of the support post side arm slide mechanism 12 shown in FIG. 5 and FIG. 10 is a right side view of the support post side arm slide mechanism 12 shown in FIG. 9.

As shown in FIG. 9, a suspended type structure, of which the rollers 32 for sliding the support post side arm 2 along the support post side arc slide axis S1 have been arranged on the lower side of the support post side arm 2, can be adopted as the structure of the support post side arm slide mechanism 12. In this case, the required distance between a ceiling and the highest part of the support post side arm 2 can be shortened further since the rollers 32 do not exist in the ceiling side of the support post side arm slide mechanism 12. Moreover, the rigidity of the support post side arm slide mechanism 12 can be secured with avoiding its interference with the support post side arm 2.

Figure 11:
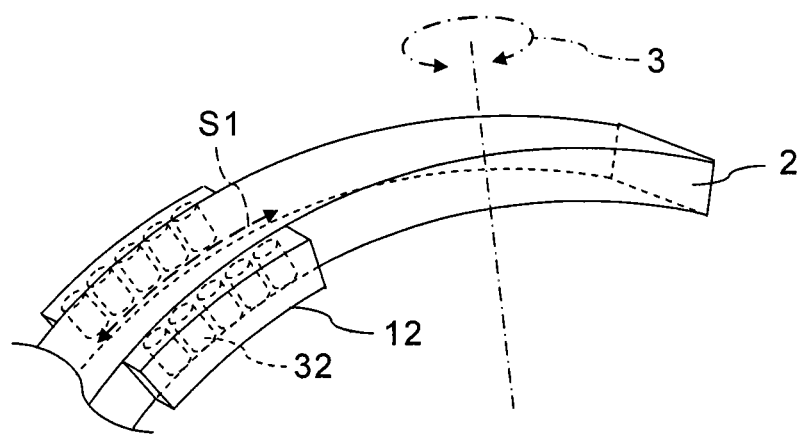
FIG. 11 is a perspective view showing the third structural example of the support post side arm slide mechanism shown in FIG. 5.

FIG. 11 is a perspective view showing the third structural example of the support post side arm slide mechanism 12 shown in FIG. 5.

As shown in FIG. 11, the structure, of which the rollers 32 for sliding the support post side arm 2 along the support post side arc slide axis S1 have been arranged on the lateral side surfaces of the support post side arm 2, can be adopted as the structure of the support post side arm slide mechanism 12. The support post side arm slide mechanism 12 including the rollers 32 is fixed to the support post circling shaft 3 with arbitrary connection members so that its interferences with the support post side arm 2 or the like do not arise.

In this case, each shape of the lateral side surfaces of the support post side arm 2 contacting with the rollers 32 is not a curved rectangle but a planar surface surrounded with two arcs and two straight lines, i.e., a planar form derived by cutting a small sector from a large sector. Therefore, the positions of the multiple rollers 32 in the vertical direction may be changed along the lateral side surfaces of the support post side arm 2 as illustrated in FIG. 11. Moreover, the multiple rollers 32 may be arranged in nonparallel so that the rotation axes become radially-arranged. Alternatively, the multiple rollers 32, each having a sufficiently long length for covering the locus of the lateral side surface of the support post side arm 2, may be arranged in parallel so that their positions in the vertical direction become similar.

When such a structure is adopted, the spaces for arranging the rollers 32 in the upper side and the lower side of the support post side arm slide mechanism 12 become unnecessary. Therefore, the required distance between a ceiling and the highest part of the support post side arm 2 can be shortened further. In addition, the rigidity of the support post side arm slide mechanism 12 can be secured with avoiding its interference with the support post side arm 2.

Especially, in the case of preparing an offset between the support post side arm slide mechanism 12 and the support post circling shaft 3, the support post side arm slide mechanism 12 is required to slide the support post side arm 2 with a sufficient rigidity. Accordingly, the rollers 32 may be arranged on at least one lateral side surface of the support post side arm 2 in addition to at least one of the upper side and the lower side of the support post side arm 2. That is, a sufficient rigidity can be secured when a structure which guides the support post side arm 2 by the rollers 32 from two directions, of at least one of the upper and lower directions and at least one of the lateral side directions, of the support post side arm 2 is adopted as the structure of the support post side arm slide mechanism 12.

Note that, each of the structures illustrated in from FIG. 8 to FIG. 11 and other various structures can surely be adopted also as a structure of the support post side arm slide mechanism 12 in the first embodiment.

Third Embodiment

Figure 12:
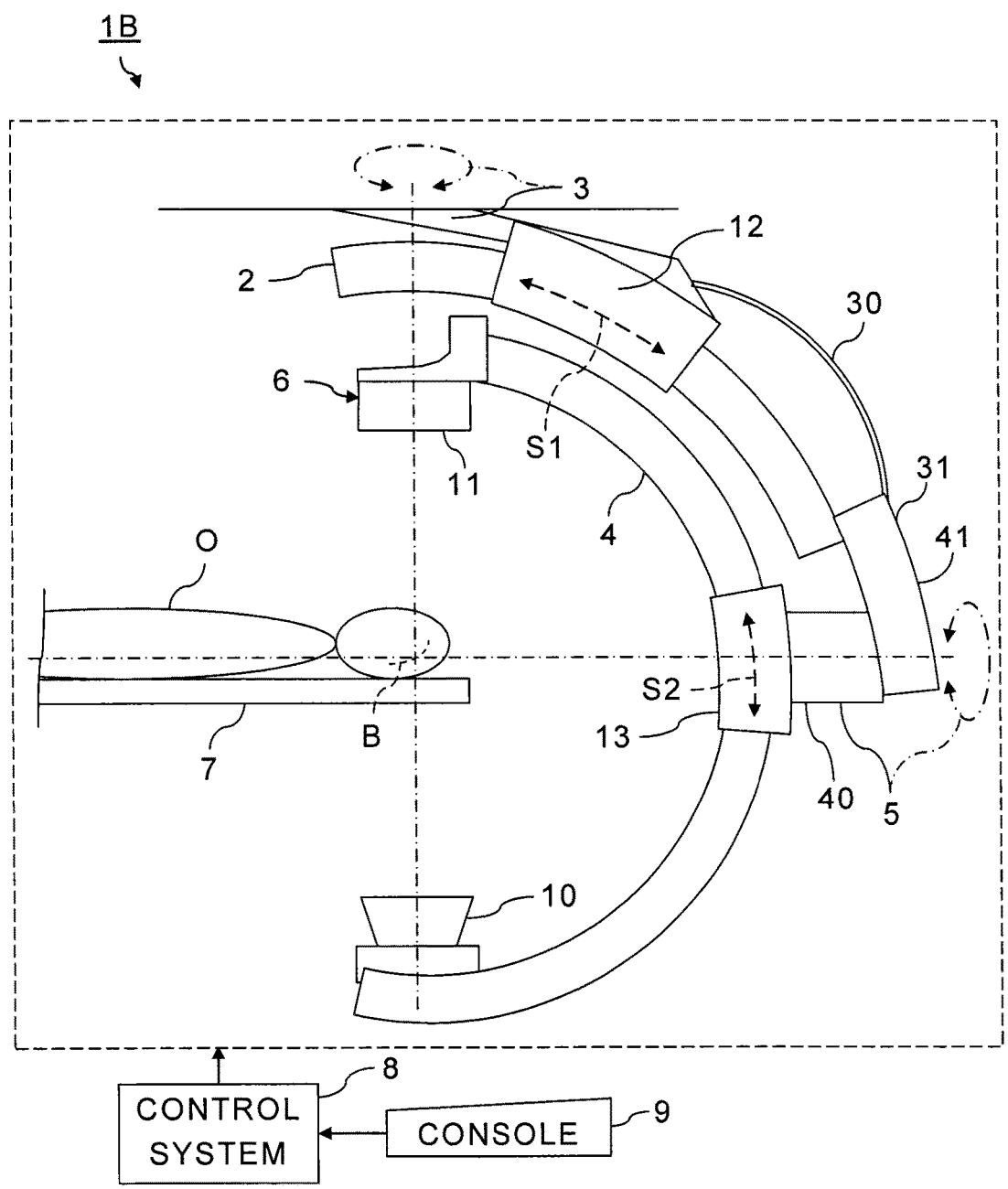
FIG. 12 is a structural view of an X-ray diagnostic apparatus according to the third embodiment of the present invention.

FIG. 12 is a structural view of an X-ray diagnostic apparatus according to the third embodiment of the present invention.

The X-ray diagnostic apparatus 1B in the third embodiment shown in FIG. 12 is different from the X-ray diagnostic apparatus 1A in the second embodiment in point that a rotating shaft holding part 31 as the second holding part for holding the C-shaped arm main rotating shaft 5 is connected with the support post side arm 2, on its side surface which does not intersect with the support post side arc slide axis S1. Since other configurations and actions of the X-ray diagnostic apparatus 1B in the third embodiment do not differ from those of the X-ray diagnostic apparatus 1A in the second embodiment substantially, same signs are attached to the same elements and explanation thereof is omitted.

In the second embodiment, the rotating shaft holding part 31 holding the C-shaped arm main rotating shaft 5 has been connected with the end face, intersecting with the support post side arc slide axis S1, of the support post side arm 2. Meanwhile, in the third embodiment, the rotating shaft holding part 31 holding the C-shaped arm main rotating shaft 5 is connected with a side surface, which does not intersect with the support post side arc slide axis S1, of the support post side arm 2. In the illustrated example, the rotating shaft holding part 31 has been connected with the outer surface side of the support post side arm 2. However, the rotating shaft holding part 31 may be connected with any of the side surfaces in the four directions. However, it is most effective to connect the rotating shaft holding part 31 with the outer surface side of the support post side arm 2, as illustrated, from a viewpoint of effective use of a space.

In this case, when the rotating shaft holding part 31 is considered to be a part of the support post side arm 2, the support post side arm 2 has not a simple arc form but a form flexural at the connection part with the rotating shaft holding part 31. As a result, the height of the lowest part of the support post side arm 2 at the initial position can be higher. That is, the height of the support post side arm 2 itself can be lower.

Furthermore, it is preferred that a casing 41 of the rotating shaft holding part 31 is arranged so that the casing 41 shifts, in the support post side arc slide axis S1 direction, toward the support post side arm slide mechanism 12 side from the end part, of the casing 40 which protects the C-shaped arm main rotating shaft 5, in the side away from the support post side arm slide mechanism 12 in the support post side arc slide axis S1 direction. For example, a drive mechanism that composes the rotating shaft holding part 31 should be arranged at an upper position than that of the C-shaped arm main rotating shaft 5.

Figure 13:
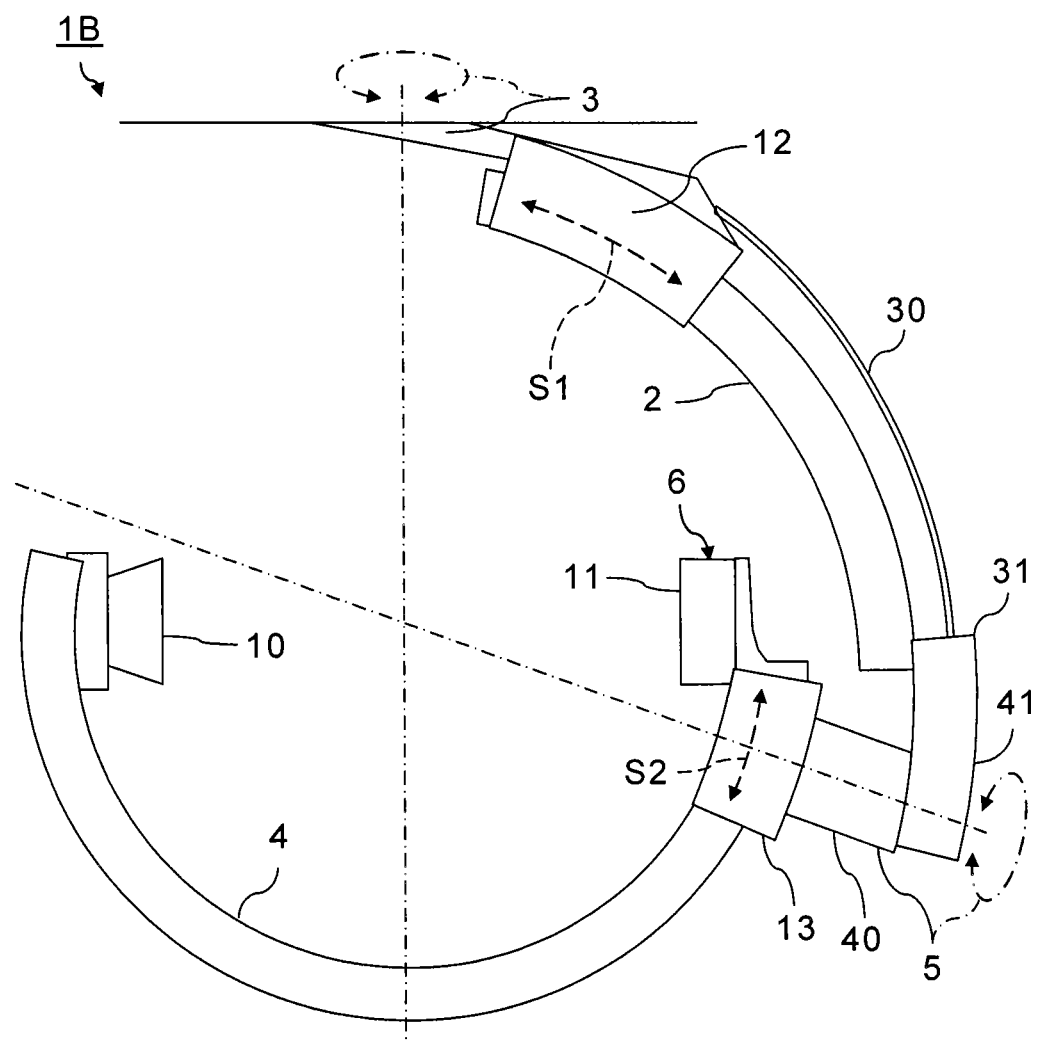
FIG. 13 is a view showing a state where the end part, in the floor side, of the support post side arm shown in FIG. 12 has approached a floor.

FIG. 13 is a view showing a state where the end part, in the floor side, of the support post side arm 2 shown in FIG. 12 has approached a floor.

When the casing 41 of the rotating shaft holding part 31 is arranged at a position higher than that of the casing 40 of the C-shaped arm main rotating shaft 5, interference by the rotating shaft holding part 31 with a floor can be avoided even when the end part in the floor side of the support post side arm 2 approaches the floor, as shown in FIG. 13.

Consequently, in the third embodiment, even in a room having a still lower ceiling, the support post side arm 2 and the C-shaped arm 4 do not interfere with a floor, and the X-ray diagnostic apparatus 1B can safely be installed. Moreover, the C-shaped arm 4 can be held, by the C-shaped arm main rotating shaft 5, at a position closer to the center of the support post side arm 2. Therefore, the rigidity of the support post side arm 2 can be secured, and the flexure amount of the support post side arm 2 can be reduced. As a result, weight saving of the support post side arm 2 can be attained.

Other Embodiments

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

Each embodiment mentioned above shows an example that the support post side arm 2 as the first arm 2 is attached to a ceiling through the support post circling shaft 3. However, the first arm 2 may be attached to a wall or a floor in an imaging room, for example. Specifically, the first arm 2 may be attached to a wall through the first rotating shaft 3. Alternatively, the first arm 2 may also be placed on a floor through the first rotating shaft 3. That is, the first arm 2 can be attached to a ceiling, a wall, or a floor using the first rotating shaft 3 as a support post.

Moreover, desired driving shafts and driving mechanisms, such as a driving shaft and a driving mechanism for moving the first rotating shaft 3 in parallel, a driving shaft and a driving mechanism for moving the X-ray detector 11 in parallel in the direction perpendicular to an X-ray incidence plane, and the like, can be prepared depending on situations.

Furthermore, the respective numbers of arms, rotation axes, and slide axes may be changed. In also that case, arms of which at least one arm slides along an arc slide axis by the slide guide mechanism 22 having the holding structure that the multiple balls 21 roll on the arc rail 20 as illustrated in FIG. 3 can be installed in an X-ray diagnostic apparatus. In this case, an arm slid by the slide guide mechanisms 22 or another arm can be rotated by at least one rotation shaft. Moreover, the imaging system 6 including the X-ray generating part 10 and the X-ray detector 11 can also be attached to an arm slid by the slide guide mechanism 22 or another arm. Furthermore, multiple imaging systems 6 may also be attached to corresponding arms. In this case, the X-ray diagnostic apparatus 1, 1A, or 1B becomes a biplane type.

Note that, when each of the first arm 2 and the second arm 4 is configured to slide as the embodiments mentioned above, an interference region by the first arm 2 and the second arm 4 can be reduced. That is, it is avoidable that extremely protruding parts arise.

Moreover, the controls by the interlocking operational mode and the independent operational mode can be designated also in an X-ray diagnostic apparatus having another structure. In that case, multiple arms are prepared in the X-ray diagnostic apparatus. Then, at least one of the multiple arms is configured to slide along an arc slide axis. Furthermore, an arm that can slide along a slide axis or at least one of the other arms is configured to rotate around a rotation axis by a rotation shaft. Then, the imaging system 6 including the X-ray generating part 10 and the X-ray detector 11 is attached to a slidable arm or at least one of the other arms among the multiple arms. Moreover, a control system that performs imaging of an object O by controlling the multiple arms and the imaging systems 6 is installed in the X-ray diagnostic apparatus.

Then, the imaging function by the interlocking operational mode and the independent operational mode can be installed in an X-ray diagnostic apparatus by configuring the control system so as to control the multiple arms and the imaging system 6 with switching the first mode, in which each of the multiple arms independently starts to move and stops, and the second mode, in which the multiple arms simultaneously start to move at the time of a movement start of the imaging system 6 while the multiple arms simultaneously stop at the time of a stop of the imaging system 6.

What is claimed is:

1. An X-ray diagnostic apparatus comprising:
  a first arm rotating around a first rotating axis and sliding along a first arc-like rail relatively to the first rotating axis;
  a second arm rotating around a second rotating axis fixed to said first arm and sliding along a second arc-like rail relatively to the second rotating axis;
  an imaging system including an X-ray generating part and an X-ray detector, the X-ray generating part and the X-ray detector being attached to said second arm;
  a slide mechanism sliding said first arm along the first rail, said slide mechanism being arranged at a position having an offset from the first rotating axis; and a control circuit configured to control the first arm and the second arm by switching between a first mode and a second mode, wherein each of the first arm and the second arm are independently started to move and stop relative to each other in the first mode, and the first arm and the second arm are moved interlocking with each other in the second mode.

2. An X-ray diagnostic apparatus of claim 1, wherein said slide mechanism is configured to be able to move said first arm in both a positive direction and a negative direction in a direction of the first rail in a state in which the second rotating axis is substantially perpendicular to the first rotating axis.

3. An X-ray diagnostic apparatus of claim 1, further comprising:

a first holding part suspending said first arm and said second arm, said first holding part being arranged on a ceiling and connected with said slide mechanism.

4. An X-ray diagnostic apparatus of claim 1, further comprising:

a second holding part for holding the second rotating axis, said second holding part being connected with said first arm in a side surface side of said first arm which does not intersect the first rail.

5. An X-ray diagnostic apparatus of claim 1, further comprising:

a second holding part for holding the second rotating axis, said second holding part being connected with an end surface of said first arm, the end surface intersecting the first rail.

6. An X-ray diagnostic apparatus of claim 4, wherein said second holding part is arranged to shift, in a direction of the first rail, toward said slide mechanism from an end part of a casing for shielding the second rotating axis, the end part being in a side distant from said slide mechanism in the direction of the first rail.

7. An X-ray diagnostic apparatus of claim 1, wherein said first arm is attached to a ceiling, a wall surface or a floor, using the first rotating axis as a support post.

8. An X-ray diagnostic apparatus of claim 1, wherein at least said first arm is configured to slide along the first rail by a slide guide mechanism having a holding structure in which balls roll on at least one arc-like rail.

9. An X-ray diagnostic apparatus of claim 1, wherein said first arm slides in a slide range along the first rail and said second arm slides in another slide range along the second rail, the slide range of said first arm being shorter than the slide range of said second arm.

10. An X-ray diagnostic method comprising:

driving a first arm rotating around a first rotating axis and sliding along a first arc-like rail relatively to the first rotating axis;

driving a second arm rotating around a second rotating axis fixed to said first arm and sliding along a second arc-like rail relatively to the second rotating axis;

imaging an object using an imaging system including an X-ray generating part and an X-ray detector, the X-ray generating part and the X-ray detector being attached to said second arm; and controlling the first arm and the second arm by switching between a first mode and a second mode, wherein each of the first arm and the second arm are independently started to move and stop relative to each other in the first mode, the first arm and the second arm are moved interlocking with each other in the second mode, and said first arm is slid along the first rail by a slide mechanism arranged at a position having an offset from the first rotating axis.

11. An X-ray diagnosis apparatus comprising:

a first arm rotating around a first rotating axis and sliding along a first arc-like rail relatively to the first rotating axis;

a second arm rotating around a second rotating axis fixed to said first arm and sliding along a second arc-like rail relatively to the second rotating axis;

an imaging system including an X-ray generating part and an X-ray detector, the X-ray generating part and the X-ray detector being attached to said second arm;

a slide mechanism sliding said first arm along the first rail, said slide mechanism being arranged at a position having an offset from the first rotating axis; and a holding part for holding the second rotating axis, said holding part being connected with said first arm in a side surface side of said first arm which does not intersect the first rail.

12. The X-ray diagnostic apparatus of claim 11, wherein said holding part is arranged to shift, in a direction of the first rail, toward said slide mechanism from an end part of a casing for shielding the second rotating axis, the end part being in a side distant from said slide mechanism in the direction of the first rail.

* * * * *